United States Patent
Amano

(10) Patent No.: US 6,821,255 B2
(45) Date of Patent: Nov. 23, 2004

(54) MERIDIAN POINT-PROBING DEVICE AND CURATIVE EFFECT-DETERMINING DEVICE

(75) Inventor: Kazuhiko Amano, Yokohama (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 10/224,370

(22) Filed: Aug. 21, 2002

(65) Prior Publication Data

US 2003/0125631 A1 Jul. 3, 2003

(30) Foreign Application Priority Data

Aug. 22, 2001 (JP) ........................................ 2001-251876

(51) Int. Cl.[7] ................................................ A61B 5/00
(52) U.S. Cl. ...................................... 600/500; 600/548
(58) Field of Search ................................ 600/485–503, 600/548

(56) References Cited

U.S. PATENT DOCUMENTS

| | | | | |
|---|---|---|---|---|
| 3,207,151 A | * | 9/1965 | Takagi | ........................ 600/547 |
| 4,160,447 A | * | 7/1979 | Teshima et al. | ............. 600/548 |
| 4,408,617 A | * | 10/1983 | Auguste | ...................... 600/548 |
| 4,556,064 A | | 12/1985 | Pomeranz et al. | |
| 5,144,554 A | | 9/1992 | Zhang et al. | |
| 5,730,138 A | | 3/1998 | Wang | |
| 6,248,064 B1 | | 6/2001 | Gopinathan et al. | |
| 6,306,160 B1 | * | 10/2001 | Nidetzky | ..................... 607/89 |

FOREIGN PATENT DOCUMENTS

| | | | | |
|---|---|---|---|---|
| DE | 198 05 939 A1 | | 8/1999 | |
| DE | 19805939 | * | 8/1999 | ................. 600/500 |
| DE | 199 08 853 A1 | | 9/2000 | |
| DE | 19908853 | * | 9/2000 | ................. 600/481 |
| EP | 0689855 | * | 6/1994 | .................... 607/1 |
| WO | WO 97/24980 | | 9/1997 | |

OTHER PUBLICATIONS translation of German Patent 198 05 939.*

* cited by examiner

Primary Examiner—Robert L. Nasser
(74) Attorney, Agent, or Firm—Oliff & Berridge, PLC

(57) ABSTRACT

A meridian point-probing device includes a pulse wave-detecting unit for detecting pulse waves, a stimulation unit having an end that stimulates a position of skin of a trial subject, a memory unit for storing pulse waveforms detected by the pulse wave-detecting unit before and after the stimulation of the position by the stimulation unit, and a meridian point determination unit for determining whether the stimulation position is a meridian point, according to the pulse waveforms stored in the memory unit. The position of the meridian point can be objectively determined with high reproducibility.

3 Claims, 9 Drawing Sheets

[FIG. 1]
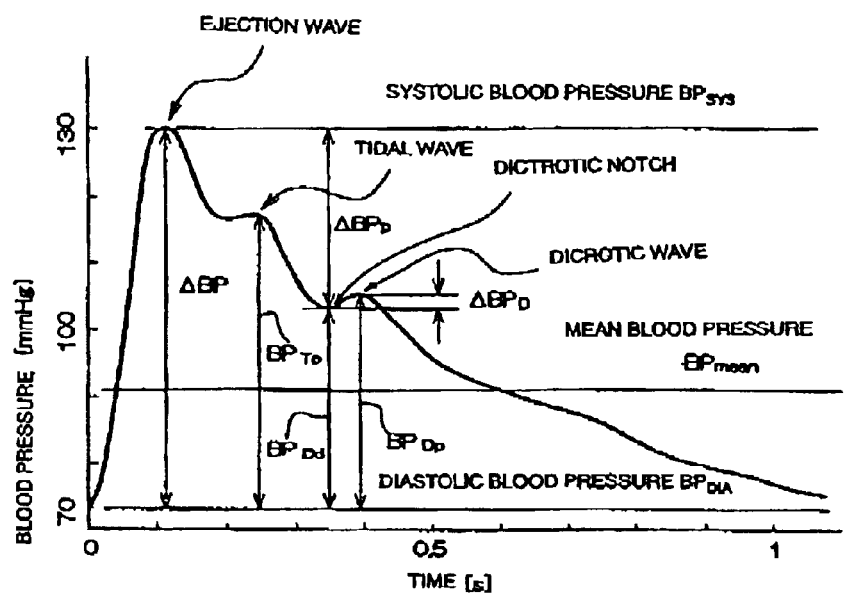

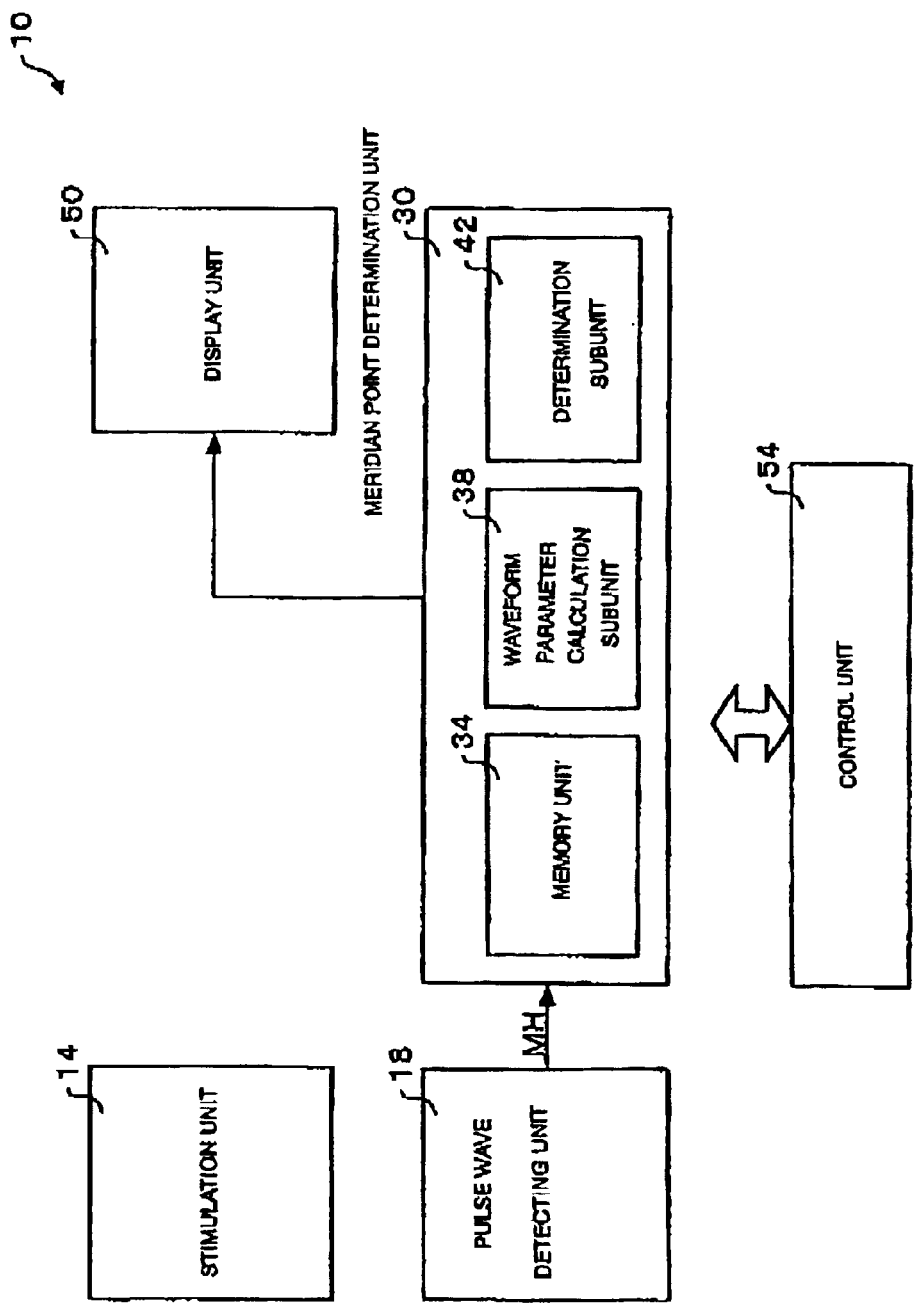

[FIG. 3]
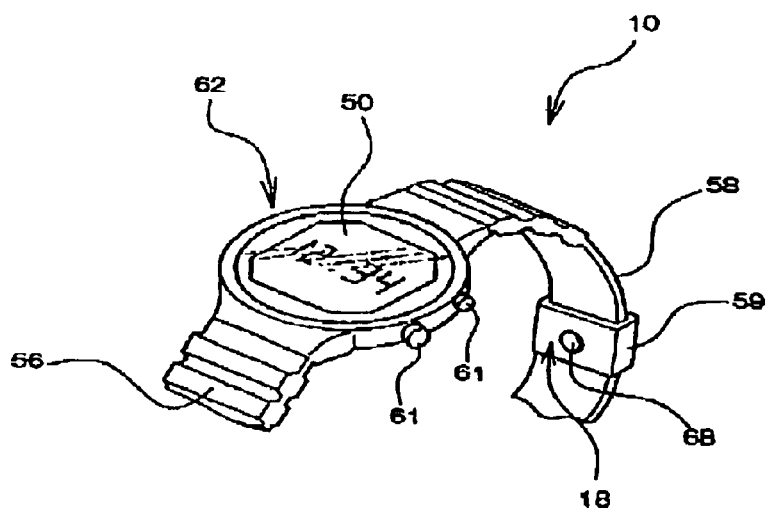
[FIG. 4]
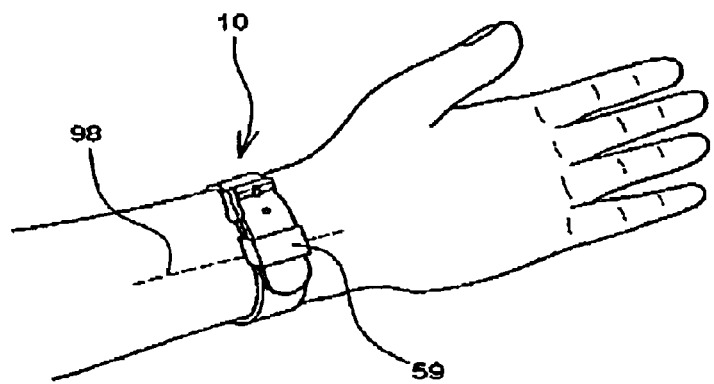

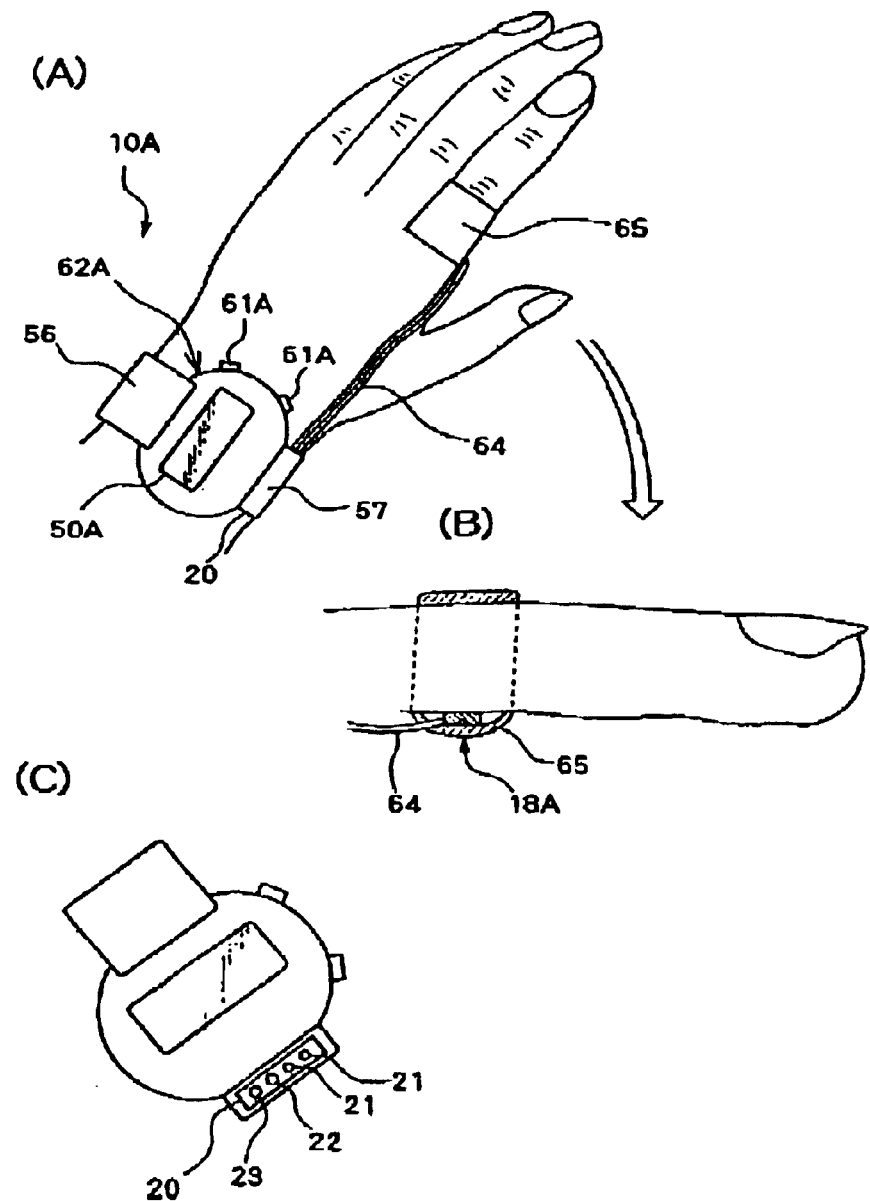
[FIG. 5]

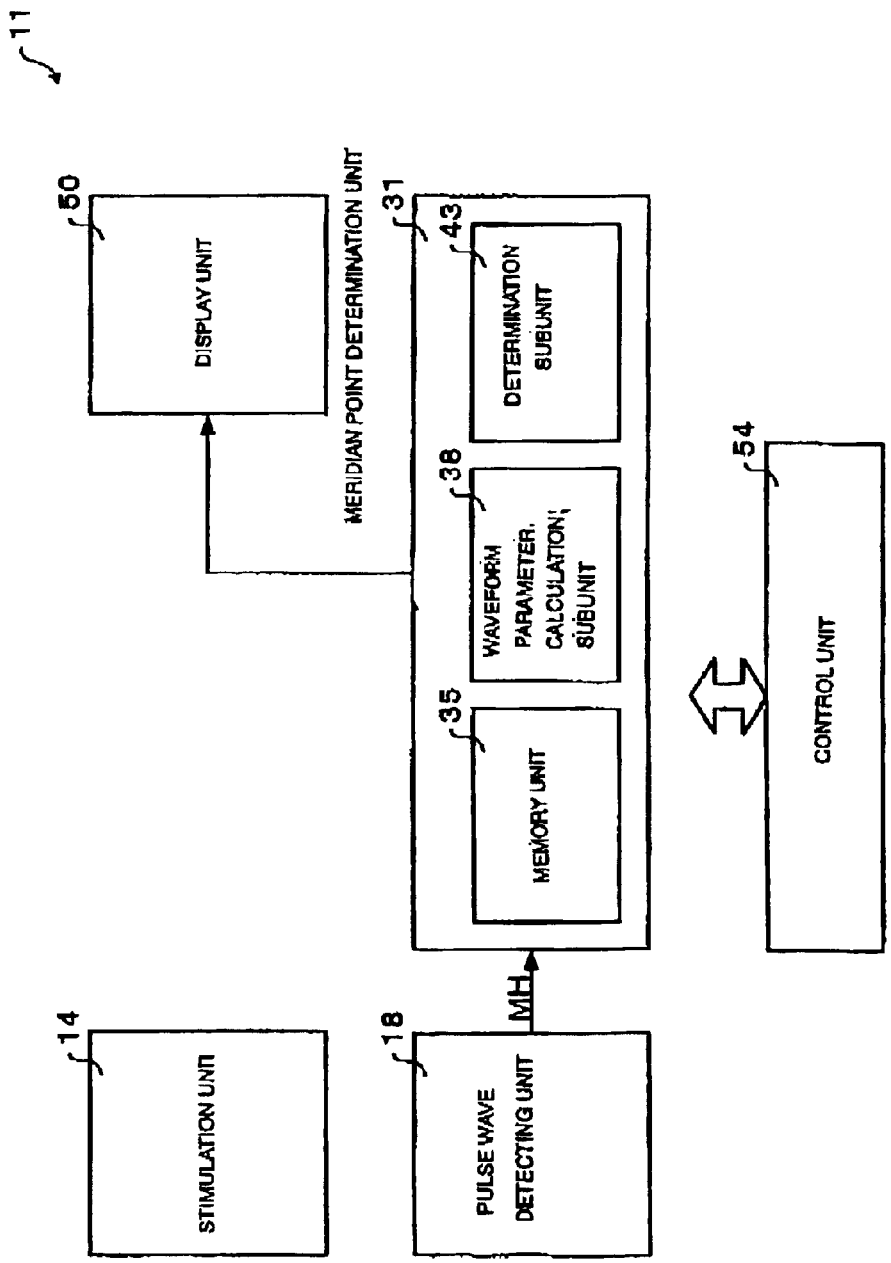
[FIG. 6]

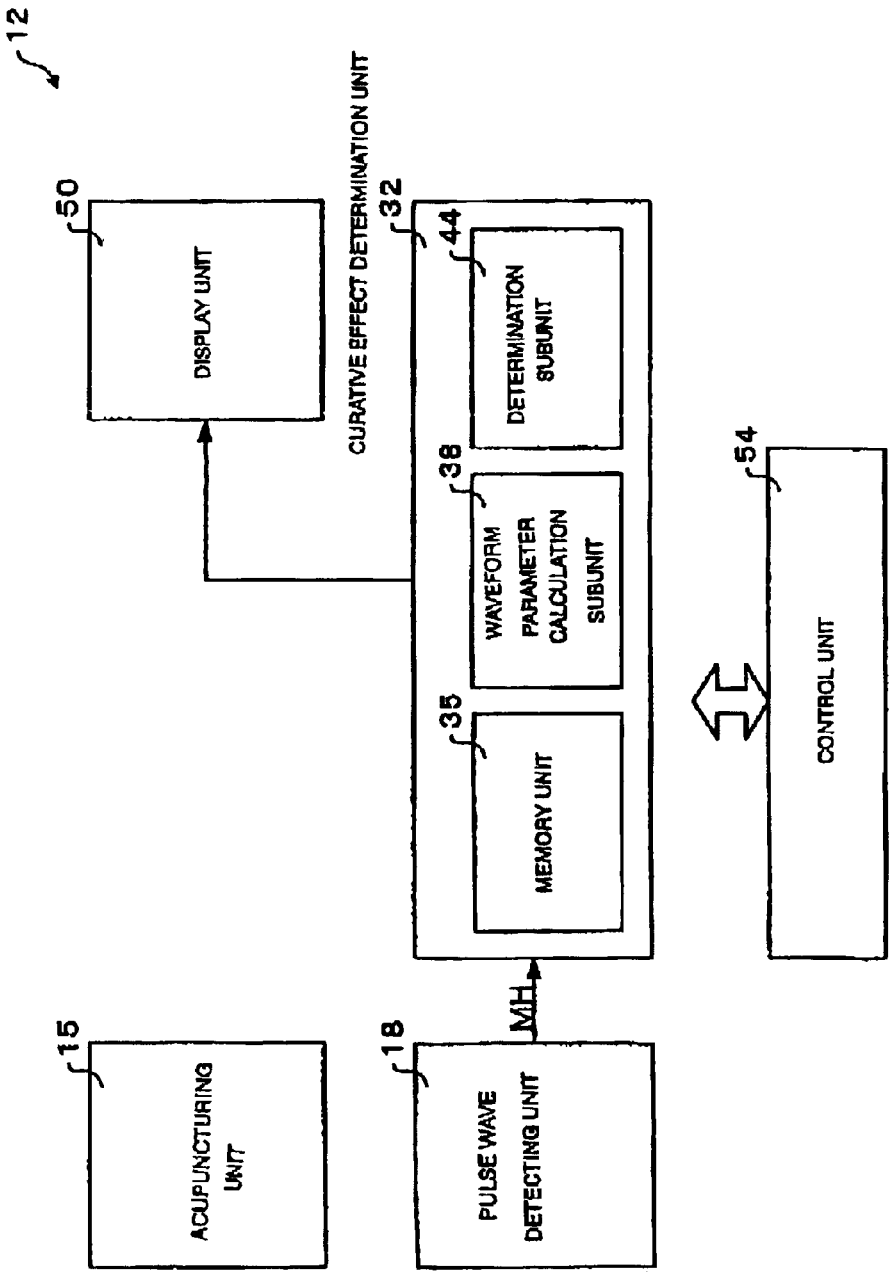

[FIG. 8]
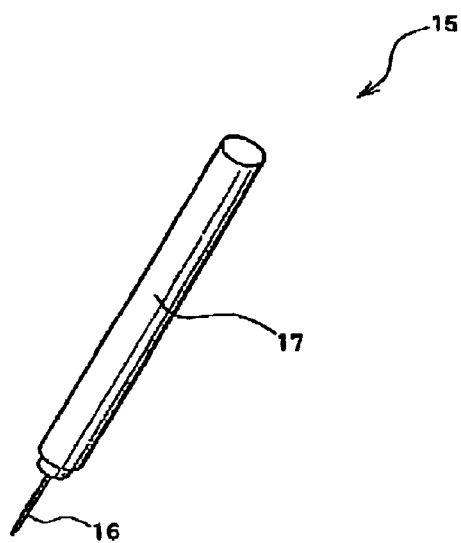

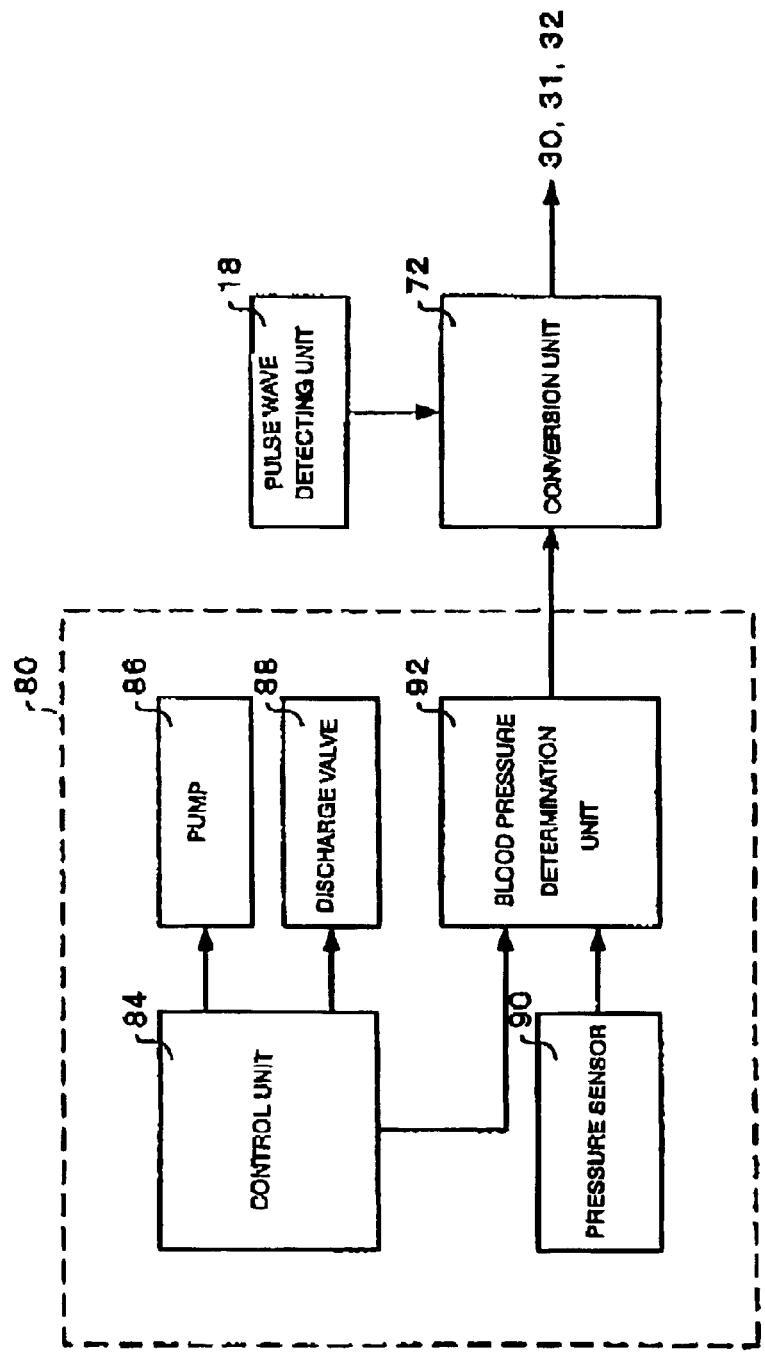
[FIG. 9]

[FIG. 10]
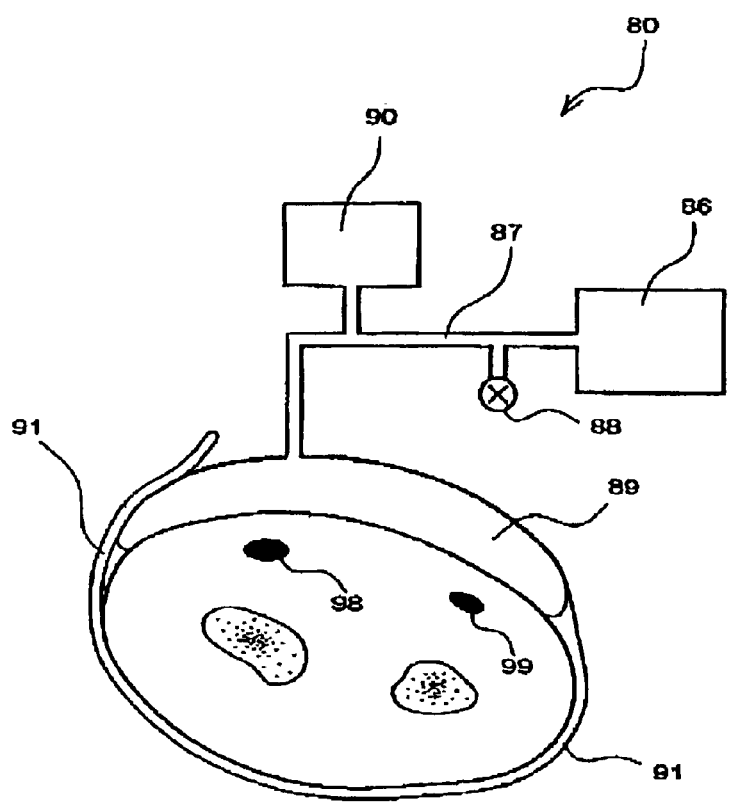

MERIDIAN POINT-PROBING DEVICE AND CURATIVE EFFECT-DETERMINING DEVICE

FIELD OF THE INVENTION

The present invention relates to a meridian point-probing device and a curative effect-determining device, which relate to meridian points ("tsubo" in Japanese) in oriental medicine.

DESCRIPTION OF RELATED ART

In acupuncture and moxibustion therapy, acupuncture and/or moxibustion is applied to spots called meridian points (tsubo) in oriental medicine for therapy. It is known that the curative effect largely depends on whether such therapy is performed at proper meridian points. Thus, it is important to determine proper meridian points in the acupuncture and moxibustion therapy.

However, in current acupuncture and moxibustion therapy, the meridian points are subjectively determined based on rough positions in a "keiraku" (energy system) diagram that is shown in many oriental medicine documents and by intuition and trial therapy according to clinical experiences. Accordingly, the meridian points have been determined subjectively without reproducibility The effects of the acupuncture and moxibustion therapy that targets the above-determined meridian points are also confirmed by a diagnostic process with an interview to a patient and pulse diagnosis called "myakushin" (sphygmopalpation) by an acupuncture and moxibustion therapist. Thus, the effects are also determined subjectively. In the pulse diagnosis, the therapist touches the radial artery of the patient to observe the pulse state.

A commercially available meridian point-probing device identifies a point having a lower contact resistance than that of its peripheries as a meridian point, but the results are unreliable.

SUMMARY OF THE INVENTION

An object of the present invention is to provide a meridian point-probing device and a curative effect-determining device having the following advantages:

A. Capable of detecting meridian points objectively and reproducibly and

B. Capable of determining the effects of the acupuncture and moxibustion therapy objectively.

(1) A meridian point-probing device according to the present invention includes a pulse wave-detecting unit which detects pulse waves, a stimulation unit having an end that stimulates a position of skin of a trial subject, a memory unit which stores pulse waveforms detected by the pulse wave-detecting unit before and after the stimulation of the position by the stimulation unit, and a meridian point determination unit which determines whether the stimulated position is a meridian point, according to the pulse waveforms stored in the memory unit.

According to the present invention, the pulse wave-detecting unit detects pulse waveforms before and after the stimulation unit stimulates a position, the memory unit stores the pulse waveforms, and the meridian point determination unit determines whether the position stimulated by the stimulation unit is a meridian point according to the pulse waveforms. The position of the meridian point can thereby be objectively determined with high reproducibility.

(2) A meridian point-probing device according to the present invention includes a pulse wave-detecting unit which detects pulse waves a stimulation unit having an end that stimulates skin of a trial subject, a memory unit which stores pulse waveforms detected by the pulse wave-detecting unit after the stimulation of a plurality of positions of the skin of the trial subject by the stimulation unit, and a meridian point determination unit which determines whether each of the stimulated positions is a meridian point, according to the pulse waveforms stored in the memory unit.

According to the present invention, the pulse wave detecting unit detects pulse waveforms after the stimulation unit stimulates a plurality of positions, the memory unit stores the pulse waveforms, and the meridian point determination unit determines whether each of the positions stimulated by the stimulation unit is a meridian point according to the corresponding pulse waveform. The positions of the meridian points can thereby be objectively determined with high reproducibility.

(3) The meridian point determination unit may include a waveform parameter calculation subunit that calculates a parameter on the pulse waveforms and determines whether the stimulated position is a meridian point, according to the parameter.

(4) The waveform parameter calculation subunit may calculate a pulse pressure that is a differential pressure between a systolic blood pressure and a diastolic blood pressure, a post-ejection pressure that is a differential pressure between a blood pressure at a dicrotic notch and the systolic blood pressure, a dicrotic wave height that is a differential pressure between the blood pressure at the dicrotic notch and a maximum blood pressure of the dicrotic wave, an post-ejection pressure ratio that corresponds to the post-ejection pressure normalized by the pulse pressure, a dicrotic wave height ratio that corresponds to the dicrotic wave height normalized by the pulse pressure, a tidal wave height ratio that corresponds to the tidal wave height normalized by the pulse pressure wherein the tidal, wave height is a differential pressure between the blood pressure of the post-ejection pressure and a maximum blood pressure of a tidal wave, or a pulse from the pulse waveforms stored in the memory unit.

(5) A curative effect-determining device according to the present invention includes a pulse wave-detecting unit which detects pulse waves, an acupuncture unit having an acuminate tip for performing an acupuncture treatment, a memory unit which stores pulse waveforms detected by the pulse wave-detecting unit before and after the acupuncturing treatment by the acuminate tip, and a curative effect determination unit which determines the curative effect of the acupuncturing treatment, according to the pulse waveforms stored in the memory unit.

According to the present invention, the pulse wave-detecting unit detects pulse waveforms before and after the acupuncturing treatment by the acupuncture unit, the memory unit stores the pulse waveforms, and the curative effect determination unit determines the effect of the acupuncturing treatment by the acupuncture unit according to the pulse waveforms stored in the soft magnetic assist film. The effect of the acupuncturing treatment can thereby be objectively determined.

(6) The curative effect determination unit may include a waveform parameter calculation subunit that calculates a parameter on the pulse waveforms and determines the curative effect of the acupuncturing treatment by the acuminate tip according to the parameter.

(7) The waveform parameter calculation subunit may calculate a pulse pressure that is a differential pressure between a systolic blood pressure and a diastolic blood pressure a post-ejection pressure that is a differential pressure between a blood pressure at a dicrotic notch and the systolic blood pressure, a dicrotic wave height that is a differential pressure between the blood pressure at the dicrotic notch and a maximum blood pressure of the dicrotic wave, an post-ejection pressure ratio that corresponds to the post-ejection pressure normalized by the pulse pressure, a dicrotic wave height ratio that corresponds to the dicrotic wave height normalized by the pulse pressure, a tidal wave height ratio that corresponds to the tidal wave height normalized by the pulse pressure wherein the tidal wave height is a differential pressure between the blood pressure of the post-ejection pressure and a maximum blood pressure of a tidal wave, or a pulse from the pulse waveforms stored in the memory unit.

BRIEF DESCRIPTION OP THE DRAWINGS

FIG. 1 is a graph of a typical blood-pressure waveform in an artery;

FIG. 2 is a block diagram of a functional configuration of a meridian point-probing device according to Embodiment A FIG. 3 is an outline view other than a stimulation unit of the meridian point-probing device according to Embodiment FIG. 4 is an isometric view of the meridian point-probing device shown in FIG. 3 that is worn on a wrist;

FIGS. 5(A), 5(B), and 5(C) are outline views other than a stimulation unit of a meridian point-probing device according to a modification;

FIG. 6 is a block diagram of a functional configuration of a meridian point-probing device according to Embodiment B;

FIG. 7 is a block diagram of a functional configuration of a meridian point-probing device according to Embodiment C;

FIG. 8 is an isometric view of an exemplary acuminate tip;

FIG. 9 is a block diagram of a functional configuration and an additional part of a blood pressure measuring unit and FIG. 10 is a schematic view illustrating a measurement of blood pressure by the blood pressure measuring unit.

DESCRIPTION OF THE PREFERRED EMBODIMENTS

Preferred embodiments of the present invention will now be described in further detail with reference to the drawings.
1. Fundamental Principle FIG. 1 is a graph of a typical blood-pressure waveform in an artery, for example, a radial artery. As shown in this drawing, a blood pressure waveform in the artery has an ejection wave having the highest peak, a tidal wave having the second highest peak, and a dicrotic wave having the third highest peak. The minimum point or inflection point between the tidal wave and the dicrotic wave is called a dicrotic notch. The peak of the ejection wave corresponds to the systolic blood pressure (maximum pressure) $BP_{sys}$ in the waveform. The diastolic blood pressure $BP_{dia}$ corresponds to the minimum blood pressure in the waveform. A differential pressure between the systolic blood pressure $BP_{sys}$ and the diastolic blood pressure $BP_{dia}$ is called a pulse pressure $\Delta BP$. The mean blood pressure $BP_{mean}$ is obtained by time-averaging the integral value of the blood pressure waveform.

In this specification, a differential pressure between the systolic blood pressure $\Delta BP_{sys}$ and the blood pressure at the dicrotic notch is called a post-ejection pressure $\Delta BP_P$; a differential pressure between the blood pressure at the dicrotic notch and the maximum blood pressure of the dicrotic wave is called a dicrotic wave height $\Delta BP_D$; and the differential pressure between the diastolic blood pressure $BP_{dia}$ and the maximum blood pressure of the tidal wave is called a tidal wave height $\Delta BP_{TP}$.

Meanwhile nifedipine, a calcium antagonist having vasodilatation, is known to have a pharmacological action that temporarily improves distensibility of blood vessel. This action is similar to a physiological state in which parasympathetic nerve dominantly works as a result of suppression of the activity of sympathetic nerve.

The present inventors measured the post-ejection pressures $\Delta BP_P$ (mmHg) of a plurality of trial subjects before and after nifedipine was administrated. Table 1 shows the results, wherein the post-ejection pressure $\Delta BP_P$ (mmHg) before administration was obtained by arithmetic average of pulse waveforms of the radial artery one hour before administration, and the post-ejection pressure $\Delta BP_P$ (mmHg) after administration was obtained by arithmetic average of pulse waveforms of the radial artery one hour after administration.

FIG. 1(A) shows that trial subjects A and B had no significant difference in the post-ejection pressure $\Delta BP_P$ between before and after nifedipine administration, but other four trial subjects C to F had an obvious increase in the post-ejection pressure $\Delta BP_P$ between before and after nifedipine administration. Accordingly, the post-ejection pressure $\Delta BP_P$, one parameter obtained from the radial artery pulse waveforms, is distinctly dependent on the physiological state.

Accordingly, monitoring the change in one parameter such as the post-ejection pressure $\Delta BP_P$ obtained from the radial artery pulse waveforms enables detection of a change in physiological states of trial subjects.
2. Embodiment A
2.1 Functional Configuration of Meridian Point-probing Device FIG. 2 is a block diagram of a functional configuration of a meridian point-probing device 10 according to this embodiment. As shown in the drawing, the meridian point-probing device 10 includes a stimulation unit 14, a pulse wave-detecting unit 18, a meridian point determination unit 30, a display unit 50, and a control unit 54.

The stimulation unit 14 has an end that stimulates skin of a human body.

The pulse wave-detecting unit 18, for example, has a pressure sensor and detects pulse waves generated by progressive expansion of an artery that follows left ventricular systole.

The meridian point determination unit 30 determines whether a position stimulated by the stimulation unit 14 is a meridian point according to the pulse waveforms detected by the pulse wave-detecting unit 18. For example, the meridian point determination unit 30 includes a memory unit 34, a waveform parameter calculation subunit 38, and a determination subunit 42. In other words, the meridian point determination unit 30 includes a CPU and a memory storing programs for operating the CPU.

The memory unit 34 stores the pulse waveforms detected by the pulse wave-detecting unit 18 before and after the stimulation unit 14 stimulates a position. The memory unit 34 may be any recording medium, for example, a semiconductor memory, a magnetic recording medium, or an optical recording medium.

The waveform parameter calculation subunit 38 calculates a pulse waveform parameter such as the post-ejection pressure $\Delta BP_P$ from the pulse waveforms stored in memory unit 34.

The determination subunit 42 determines whether the position stimulated by the stimulation unit 14 is a meridian point according to a parameter such as the post-ejection pressure $\Delta BP_p$ before and after the stimulation unit 14 stimulates the position.

The display unit so displays the determined results on the stimulated position by the meridian point determination unit 30 in the form of text, symbol, or graph.

2.2 Outline Configuration of Meridian Point-probing Device

For example, the meridian point-probing device 10 excluding the stimulation unit 14 may be used in the form of a wristwatch, as shown in FIGS. 3 and 4. FIG. 3 is an isometric view of the device itself, and FIG. 4 is an isometric view of the device that is worn on a wrist.

As shown in these drawings, the meridian point-probing device 10, excluding the stimulation unit 14, includes a main portion 62, a pair of bands 56 and 58 attached to the main portion 62, a sensor holder 59 movable along the band 58. The sensor holder 59 includes a pulse wave-detecting unit 18 having a protruding pressure sensor 68. The protruding pressure sensor 68 transmits signals to the main portion 62 through a connection not shown in the drawing, for example, a flexible printed circuit (PPC) board.

The main portion 62 includes at least one semiconductor integrated circuit (IC) now shown in the drawing. In this embodiment, the display unit 50 displays time information. Operating knobs 61 switches between a measuring mode for measuring pulse waveforms and a watch mode for displaying time. The operating knobs 61 are also used for inputting various data.

When the meridian point-probing device 10 is used, as shown in FIG. 4, the meridian point-probing device 10 is worn on a wrist of a trial subject like a wristwatch such that the sensor bolder 59 lies near the radial artery 98. The sensor holder 59 is slid along the band 58 so that the pressure sensor 68 of the sensor holder 59 is disposed on the radial artery 98.

When the pressure sensor 68 presses the radial artery 98 of the trial subject, pulse waves corresponding to vibrations of the vessel wall caused by a change in blood flow in the artery are transmitted from the pressure sensor 68 to the pulse wave-detecting unit 18. The meridian point-probing device 10 can thereby detect pulse waveforms. The detected pulse waveforms are substantially the same as blood pressure waveforms of the artery.

2.3 Operation of Meridian Point-probing Device

The meridian point-probing device 10 determines whether a position of a trial subject stimulated by the stimulation unit is a meridian point, according to the following operation.

The band 58 is wound around the wrist and the sensor holder 59 is fixed near the radial artery 98.

Before the stimulation unit 14 stimulates a position of the trial subject, the pressure sensor 68 of the pulse wave-detecting unit 18 detects the pulse waveform (vibration waveform of the vessel wall that follows a blood flow in an artery of the wrist such as the radial artery 98) as a pressure waveform. The pulse waveform detected by the pressure sensor 68 is stored in the memory unit 34. The waveform parameter calculation subunit 38 calculates a parameter according to the pulse waveform stored in the memory unit 34.

A portion presumed to be a meridian point is stimulated by the stimulation unit 14.

After the stimulation to the trial subject by the stimulation unit 14, the pressure sensor 68 redetects a pulse waveform. The pulse waveform detected by the pressure sensor 68 is stored in the memory unit 34. According to the pulse waveform stored in the memory unit 34, the waveform parameter calculation subunit 38 calculates a parameter of the pulse waveform such as the post-ejection pressure $\Delta BP_p$.

The determination subunit 42 determines whether the position stimulated by the stimulation unit 14 is a meridian point according to the parameter, for example, the post-ejection pressures $\Delta BP_p$ calculated by the waveform parameter calculation subunit 38 before and after the stimulation by the stimulation unit 14.

The results appear on the display unit 50, for example, including a liquid crystal display, in the form of text and graph.

2.4 Modifications of Embodiment A 2.4.1. In the above embodiment, the parameter, which is calculated by the waveform parameter calculation subunit 38 of the meridian point determination unit 30 and is used for determining whether the stimulated position is a meridian point in the determination subunit 42, is the post-ejection pressure $\Delta BP_p$. Alternatively, the parameter which is calculated in the waveform parameter calculation subunit 38 of the meridian point determination unit 30 and is used for determination in the determination subunit 42, may be the pulse pressure $\Delta BP$, which is a differential pressure between the systolic blood pressure and the diastolic blood pressure; the dicrotic wave height $\Delta BP_p$, which is a differential pressure between the blood pressure at the dicrotic notch and the maximum blood pressure of the dicrotic wave; a post-ejection pressure ratio $\Delta BP_p/\Delta BP$, which corresponds to the post-ejection pressure (–a differential pressure between the systolic blood pressure and the blood pressure at the dicrotic notch) normalized by the pulse pressure; a dicrotic wave height ratio $\Delta BP_p/\Delta BP$, which corresponds to the dicrotic wave height (–a differential pressure between the blood pressure at the dicrotic notch and the maximum blood pressure of the dicrotic wave) normalized by the pulse pressure; a tidal wave height ratio $\Delta BP_{Tp}/\Delta BP$, which corresponds to the tidal wave height (–a differential pressure between the diastolic blood pressure $\Delta BP_{dia}$ and the maximum blood pressure of the tidal wave) normalized by the pulse pressure; or a pulse.

2.4.2 In the above embodiment, the pulse wave-detecting unit detects pulse waveforms of the radial artery 98. Alternatively, the pulse wave-detecting unit may detect pulse waveforms of any appendicular or finger arteries, such as an ulnar artery of a wrist, a palmar digital artery of a finger, a brachial artery of an upper arm, or a popliteal artery of a lower limb. Alternatively, the pulse wave-detecting unit may detect pulse waveforms of any other arteries flowing near the surface, such as carotid artery and femoral artery.

2.4.3 In the above embodiment, the pulse wave-detecting unit is a pressure sensor. Since the pulse waveform is substantially the same as a change waveform of a blood flow rate, the pulse wave-detecting unit may be an optical sensor that emits light toward an artery and detects a change in reflected light intensity or transmitted light caused by the blood flow in the artery, in place of the pressure sensor.

For example, such an optical sensor is composed of a light-emitting diode (LED) and a phototransistor. The wavelength of light emerging from the LED is set near the peak wavelength of reflection or absorption of hemoglobin in the blood while the wavelength range of light received by the phototransistor is set near the peak wavelength of reflection or absorption of the hemoglobin. Thus, the received light intensity changes with the blood flow rate. The pulse waveform can thereby be detected as a change in the received light intensity.

Such an optical sensor detects pulse waves that change in response to the blood flow rate, namely, volume pulse waves as a change in the red blood count in the capillary plexus near skin and thus as a change in transmittance or reflectance of light emerging toward the skin. Thus, the optical sensor can detect pulse waves without aligning the sensor to, for example, a radial artery. Thus, the pulse wave-detecting unit including such an optical sensor can stably detect a change in the red blood count in the capillary plexus near skin as pulse waves (volume pulse waves) in a peripheral artery.

As described above, the meridian point-probing device 10 according to the present invention can use the post-ejection pressure ratio $\Delta BP_p/\Delta BP$, which corresponds to the post-ejection pressure (−a differential pressure between the maximum blood pressure and the blood pressure at the dicrotic notch) normalized by the pulse pressure (−a differential pressure between the maximum pressure and the minimum pressure), the dicrotic wave height ratio $\Delta BP_p/\Delta BP$, which corresponds to the dicrotic wave height (−a differential pressure between the blood pressure at the dicrotic notch and the maximum blood pressure of the dicrotic wave) normalized by the pulse pressure, the tidal wave height ratio $\Delta BP_{Tp}/\Delta BP$ which corresponds to the tidal wave height normalized by the pulse pressure, or the pulse, as a parameter used for determining whether the position stimulated by the stimulation unit 14 is a meridian point. Thus, the pulse wave-detecting unit does not need to detect the blood pressure itself directly. Accordingly, a pulse wave-detecting unit including a photoelectric sensor capable of detecting a waveform that is substantially the same as the waveform of the blood pressure can be used in the above meridian point-probing device.

FIGS. 5(A), 5(B), and 5(C) are outline views of a meridian point-probing device 10A including such a pulse wave-detecting unit 18A (not including the stimulation unit 14). The meridian point-probing device 10A includes a main portion 62A having a structure like a wrist watch, a cable 64 connected to a connector 20 of the main portion 62A with a connector piece 57, and the pulse wave-detecting unit 18A provided at an end of the cable 64. The main portion 62A has a wristband 56 for fixing the main portion 62A to a wrist of a trial subject.

The main portion 62A includes the connector 20. The detachable connector piece 57 at the other end of the cable 64 is connected to the connector 20.

FIG. 5(C) shows the connector 20 from which the connector piece 57 is detached. For example, the connector 20 includes connection pins 21 for connecting to the cable 64, an LED 22 for transmitting data, and a phototransistor 23.

At the surface of the main portion 62A, a display unit 50A composed of a liquid crystal panel is provided. The display unit 50A has a segment display region and a dot display region and displays a central blood pressure waveform, a central blood pressure waveform parameter, or analytical results, for example. The display unit 50A may be any other display devices in place of the liquid crystal panel.

The main portion 62A includes a central processing unit (CPU) for controlling various calculations and conversions and a memory (not shown) for storing programs for CPU operation in the interior and includes operation knobs 61A for various operations and inputting at the periphery.

As shown in FIG. 5(B) the pulse wave-detecting unit 18A is shaded by a band 65 for fixing the sensor and is fixed near the bottom of the index finger of a trial subject. Since the pulse wave-detecting unit 18A is fixed in such a manner, a abort cable 64 can be used and is not a hindrance of fixing. Since a change in blood flow rate with temperature at the bottom of a finger is smaller than that at the fingertip, the detected pulse waveform is not so affected by the environmental temperature.

2.4.4 in the above embodiment, the meridian point determination unit 30, the display unit 50, and the control unit 54 are built into the main portion 62. Any one of these units may be separated from the main portion 62 and may be electrically connected to the pulse wave-detecting unit 18 or the stimulation unit 14.

2.4.5 In the above embodiment, the display unit 50 including the liquid crystal display is used as a disclosure portion, and the display unit 50 display a text and graph. Alternatively, a printer, a voice synthetic unit, or a speaker may be used as a disclosure portion instead of or together with the display unit 50 to display the information as display, printed text, or voice.

2.5 Effects of Embodiment A

As described above, in the meridian point-probing device 10 according to this embodiment, the pulse wave-detecting detecting unit 18 detects pulse waveforms before and after the stimulation unit 14 stimulates a position, the memory unit 34 stores the pulse waveforms, and the meridian point determination unit 30 determines whether the position stimulated by the stimulation unit 14 is a meridian point according to the pulse waveforms. The position of the meridian point can thereby be objectively determined with high reproducibility.

3. Embodiment B

The meridian point-probing device in this embodiment differs from that according to Embodiment A in that the memory unit stores pulse waveforms detected by the pulse wave-detecting unit after the stimulation of a plurality of positions by the stimulation unit and the meridian point determination unit determines whether each of the stimulated positions is a meridian point, according to the pulse waveforms stored in the memory unit. The differences from Embodiment A will now be intensively described. Since other features are the same as those in Embodiment A, the description thereof is omitted. The same reference numerals are allocated to the same components in the drawings 3.1 Functional Configuration of Meridian Point-probing Device FIG. 6 is a block diagram of a functional configuration of a meridian point-probing device 11 according to this embodiment. The functional configuration of this embodiment is substantially the same as that in Embodiment A.

The operation of the meridian point determination unit, however, is partly different.

In this embodiment, the meridian point determination unit 31 stores pulse waveforms that are detected by the pulse wave-detecting unit 18 after the stimulation of a plurality of positions by the stimulation unit. The meridian point determination unit 31 includes a memory unit 35, a waveform parameter calculation subunit 38, and a determination Subunit 43.

The memory unit 35 stores the pulse waveforms a plurality of positions detected by the pulse wave-detecting unit 18 after the stimulation unit 14 stimulates these positions.

The waveform parameter calculation subunit 38 calculates a pulse waveform parameter such as a post-ejection pressure $\Delta BP_p$ from each of the pulse waveforms stored in the memory unit 35.

The determination subunit 43 determines whether each of the positions stimulated by the stimulation unit 14 is a meridian point according to a parameter corresponding to each position. For example, the determination subunit 43 compares post-ejection pressures $\Delta BP_p$ that are calculated in the waveform parameter calculation subunit 38 to determine whether each of the positions simulated by the stimulation unit 14 it a meridian point.

3.2 Outline Configuration of Meridian Point-probing Device

The outline configuration of the meridian point-probing device 10 according to this embodiment may be the same as that in Embodiment A.

3.3 Operation of Meridian Point-probing Device

The meridian point-probing device 11 determines whether each of the positions of a trial subject stimulated by the stimulation unit 14 is a meridian point, according to the following operation.

The band 59 is wound around the wrist and the sensor holder 59 is fixed near the radial artery 98.

A portion presumed to be a meridian point is stimulated by the stimulation unit 14.

After a predetermined time from the stimulation to the trial subject by the stimulation unit 14, the pressure sensor 68 redetects a pulse waveform. The pulse waveform detected by the pressure sensor 68 is stored in the memory unit 34.

The stimulation by the stimulation unit 14 and detecting and storing of the pulse waveform after the predetermined time from the stimulation are repeated for a plurality of positions.

According to the pulse waveform corresponding to each stimulated position stored the memory unit 34, the waveform parameter calculation subunit 38 calculates a parameter of the pulse waveform such as the post-ejection pressure $\Delta BP_p$. Next, the determination subunit 43 compares the parameters corresponding to the stimulated positions to determine whether each of the stimulated positions is meridian point.

The determined results appear on the display unit 50, which for example, includes a liquid crystal display device, in the form of text, symbol, or graph.

3.4 Modifications of Embodiment B 3.4.1 in the above embodiment, the memory unit stores pulse waveforms corresponding to the stimulated positions and the waveform parameter calculation subunit calculates the parameters after these pulse waveforms are stored. Alternatively, the waveform parameter calculation subunit may calculate each parameter after a pulse waveform corresponding to each of the stimulated positions is stored.

3.4.2 Each modification shown in Embodiment A may also be applied to this Embodiment.

3.5 Effects of Embodiment B

As described above, the pulse wave-detecting unit 18 detects pulse waveforms after the stimulation unit 14 stimulates a plurality of positions, the memory unit 35 stores the pulse waveforms, and the meridian point determination unit 31 determines whether each of the positions stimulated by the stimulation unit 14 is a meridian point according to the corresponding pulse waveform. The positions of the meridian points can thereby be objectively determined with high reproducibility.

4. Embodiment C

A curative effect-determining device according to this embodiment fundamentally differs from the meridian point-probing device according to Embodiment A in that the stimulation unit is replaced with an acupuncture unit and the meridian point determination unit is replaced with a curative effect determination unit. The differences from Embodiment A will now be intensively described. Since other features are the same as those in Embodiment A, the description thereof is omitted. The same reference numerals are allocated to the same components in the drawings.

4.1 Functional Configuration of Curative Effect-Determining Device

FIG. 7 is a block diagram of a functional configuration of a curative effect-determining device 12 according to this embodiment. The functional configuration of this embodiment is substantially the same as that in Embodiment A. However, the stimulation unit 14 is replaced with an acupuncture unit 15 and the meridian point determination unit 30 is replaced with a curative effect determination unit 32.

The acupuncture unit 15 has an acuminate tip used for performing an acupuncture treatment.

The curative effect determination unit 32 determines the curative effect of the acupuncture treatment, according to the pulse waveforms detected by the pulse wave-detecting unit 18 before and after the acupuncturing treatment. For example, the curative effect determination unit 32 includes a memory unit 36, a waveform parameter calculation subunit 38, and a determination subunit 44. In other words, the curative effect determination unit 32 includes a CPU and a memory storing programs for operating the CPU.

The memory unit 36 stores the pulse waveforms detected by the pulse wave-detecting unit 18 before and after the acupuncture treatment by the acupuncture unit 15. The memory unit 36 may be any recording medium, for example, a semiconductor memory, a magnetic recording medium, or an optical recording medium.

The waveform parameter calculation subunit 38 calculates a pulse waveform parameter such as the post-ejection pressure $\Delta BP_p$ from the pulse waveforms stored in the memory unit 36.

The determination subunit 44 determines the curative effect of the acupuncture treatment according to the pulse waveforms detected by the pulse wave-detecting unit 18 before and after the acupuncture treatment by the acupuncture unit 15. For example, the determination subunit 44 determines the curative effect according to a change in post-ejection pressure $\Delta BP_p$ before and after the acupuncture treatment, wherein the post-ejection pressure is one of the parameters calculated from the pulse waveforms.

The display unit 50 displays the determined results on the curative effect of the acupuncture treatment by the acupuncture unit 15 in the form of text, symbol, or graph.

4.2 Outline Configuration of Curative Effect-Determining Device

The outline configuration of the curative effect-determining device 12 is substantially the same as that in Embodiment A except that the acupuncture unit 15 is included.

FIG. 8 shows a schematic example of the acupuncture unit 1S. The acupuncture unit 15 includes an acuminate tip 16 and a holder 17 for holding the acuminate tip 16.

4.3 Operation of Curative Effect-Determining Device

The curative effect-determining device 12 determines the curative effect of the acuminate tip according to the following operation.

The band 58 is wound around the wrist and the sensor holder 59 is fixed near the radial artery 98.

Before the acupuncture treatment by the acupuncture unit 15, the pressure sensor 68 of the pulse wave-detecting unit 18 detects the pulse waveform. The pulse waveform detected by the pressure sensor 68 is stored in the memory unit 36. The waveform parameter calculation subunit 38 calculates a parameter, for example, a post-ejection pressure $\Delta BP_p$, according to the pulse waveform stored in the memory unit 36.

Next, the acupuncture unit 15 stimulates a portion of a trial subject according to the medical treatment.

After the stimulation of the position by the acupuncture unit 15, the pressure sensor 68 redetects the pulse waveform. The memory unit 36 stores the pulse waveform detected by the pressure sensor 68. The waveform parameter calculation subunit 38 calculates a parameter of the pulse waveform according to the pulse waveform stored in the memory unit 36.

Next, the determination subunit 44 determines the effect of the acupuncture treatment by the acupuncture unit 15 according to the parameters before and after the stimulation by the acupuncture unit 15.

The results appear on the display unit 50, for example, including a liquid crystal display, in the form of text and graph.

4.4 Modifications of Embodiment C 4.4.1 In the above embodiment, the parameter, which is calculated by the waveform parameter calculation subunit 38 of the curative effect determination unit 32 and is used for determining the curative effect by the determination subunit 44, is the post-ejection pressure $\Delta BP_p$. Alternatively, the parameter, which is calculated in the waveform parameter calculation subunit 38 of the curative effect determination unit 32 and is used for determination in the determination subunit 44, may be the pulse pressure $\Delta BP$, which is a differential pressure between the systolic blood pressure and the diastolic blood pressure; the dicrotic wave height $\Delta BP_D$, which is a differential pressure between the blood pressure at the dicrotic notch and the maximum blood pressure of the dicrotic wave: a post-ejection pressure ratio $\Delta BP_p/\Delta BP$, which corresponds to the post-ejection pressure (-a differential pressure between the systolic blood pressure and the blood pressure at the dicrotic notch) normalized by the pulse pressure; a dicrotic wave height ratio $\Delta BP_D/\Delta BP$, which corresponds to the dicrotic wave height (-a differential pressure between the blood pressure at the dicrotic notch and the maximum blood pressure of the dicrotic wave) normalized by the pulse pressure; a tidal wave height ratio $\Delta BP_{Tp}/\Delta BP$, which corresponds to the tidal wave height (-a differential pressure between the diastolic blood pressure $\Delta BP_{dia}$ and the maximum blood pressure of the tidal wave) normalized by the pulse pressure; or a pulse.

4.4.2 Modifications 2.4.2, 2.4.3, 2.4.4, and 2.4.5 in Embodiment A can also be applied to this embodiment.

4.5 Effects of Embodiment C.

As described above, in the curative effect-determining device 12 according to this embodiment, the pulse wave-detecting unit 18 detects pulse waveforms before and after the acupuncturing treatment by the acupuncture unit 15, the memory unit 36 stores the pulse waveforms, and the curative effect determination unit 32 determines the effect of the acupuncturing treatment by the acupuncture unit 15 according to the pulse waveforms stored in the soft magnetic assist film 36. The effect of the acupuncturing treatment can thereby be objectively determined.

5. Embodiment D

In the above embodiments, the probing of the meridian points and the determination of the curative effect are performed using pulse waveforms detected by the pulse wave-detecting unit 18 or 18A. Alternatively, a blood pressure measuring unit and a conversion unit may be included together with the pulse wave-detecting unit so that the pulse waveforms are converted into blood pressure waveforms that are used for probing the meridian points or determining the curative effect.

FIG. 9 is a block diagram showing a functional configuration of the blood pressure measuring unit 80 and a portion relating to the blood pressure measuring unit 80, namely, the relationship between the pulse wave-detecting in addition to the pulse wave-detecting units 18 and 18A shown in the above embodiments any other pulse wave-detecting units having sensors for detecting pulse waveforms may be used.

The blood pressure measuring unit 80 measures the blood pressure at the same positions that are used for detecting pulse waves by the pulse wave-detecting unit 18. An embodiment of the blood pressure measuring unit 80 will be described below in detail.

The 72 converts the pulse waveform detected by the pulse wave-detecting unit 18 into a blood pressure waveform at the position, according to the blood pressure value measured by the blood pressure measuring unit 80. For example, the conversion unit 72 converts the pulse waveform into the blood pressure waveform using the amplitude between the systolic blood pressure and the diastolic blood pressure that are measured by the blood pressure measuring unit 80. The resulting blood pressure waveform is input into the meridian point determination unit 30 or 31 or the curative effect determination unit 32 to perform determination using the blood pressure waveform instead of the pulse waveform.

FIG. 10 is a schematic view of the blood pressure measuring unit 80 for measuring the blood pressure. The blood pressure measuring unit 80 measures a blood pressure by winding a band 91 around a position for detecting the pulse wave by the pulse wave-detecting unit 18, for example, a wrist. The band 91 has a pressure bag 89 therein and is wound around the wrist such that the pressure bag 89 faces the radial artery 98.

The pressure bag 89 connects with a pump 86 and a discharge valve 88 via a pipe 87. The pump 86 and the discharge valve 88 control the volume of a liquid charged in the pressure bag 89 to control the pressuring force of the pressure bag 89 to the radial artery 98.

The pipe 87 is provided with a pressure sensor 90 for detecting the change in liquid pressure. The pressure sensor 90 detects vibration of the radial artery 98 as a change in pressure of the liquid that transmitted via the pressure bag 89 and the pipe 87. Since the pressure bag 89 lying above the radial artery 98 is pressured in response to the vibration of the radial artery 98, the pressure of the liquid in the pressure bag 89 changes in response to the vibration of the radial artery 90. Thus, the pressure sensor 90 detecting such a change in pressure can output signals corresponding to the vibration of the radial artery 98.

The blood pressure measuring unit 80, constituting a part of the configuration shown in FIG. 9, further includes a control unit 84 and a blood pressure determination unit 92, in addition to the above units.

The control unit 84 controls the operation of the pump 86 and the discharge valve 88 to cause a change in pressure of the pressure bag 89 by controlling the volume of the liquid in the pressure bag 89 so that the pressure bag 89 presses the radial artery 98 with a variable applying pressure within a predetermined range. For example, the control unit 84 includes a CPU and a memory such a semiconductor memory for storing programs for CPU operation.

The blood pressure determination unit 92 inputs a variety of pressure information from the pressure bag 89 through the control unit 84 and detection signals from the pressure sensor 90 at each pressure and determines the maximum blood pressure and the minimum blood pressure according to the input information. For example, the blood pressure determination unit 92 includes a CPU and a memory for storing programs for CPU operation.

The operation of blood pressure measurement of the blood pressure measuring unit 80 will now be described.

The cuff band 91 is wound around a wrist such that the pressure bag 89 lies above the radial artery 98.

The pump 86 and the discharge valve 98 are controlled by the control unit 84 to control the volume of the liquid in the pressure bag 89. The applying pressure in the pressure bag 89 is thereby changed. The pressure bag 89 presses the radial artery at a variable applying pressure within a predetermined range. Specifically, the control unit 84 controls the applying pressure of the pressure bag 89 within the range of, for example, 250 to 20 mg, the range being slightly wider than a typical blood pressure range.

The pressure sensor 90 for detecting the vibration of the radial artery 98 detects signals corresponding to the vibration of the vascular wall due to blood flow in the blood vessel which is narrowed by each applying pressure from the pressure bag 89. The results are stored in the blood pressure determination unit 92 together with the corresponding applying pressure from the pressure bag 89. The applying pressure from the pressure bag 89 is transmitted from the control unit 84 for controlling the applying pressure to the blood pressure determination unit 92.

After a sufficient number of data that covers the above applying pressure range of the pressure bag 89 is sampled, the blood pressure determination unit 92 determines the blood pressure. The highest applying pressure from the pressure bag 89 that is detected as the vibration caused by the blood flow in the blood vessel in the narrowed state by the pressure sensor 90 is defined as the maximum blood pressure, whereas the lowest applying pressure from the pressure bag 89 that is detected as the vibration caused by the blood flow in the blood vessel in the narrowed state by the pressure sensor 90 is defined as the minimum blood pressure. The principle of this blood pressure measurement is the same as that of stethoscopy in which the blood pressure is determined by monitoring vibration of the vessel wall caused by blood flow in the narrowed blood vessel at an abaxial side of the artery pressed by a wrist band.

The embodiments according to the present invention have been described above. The present invention, however, is not limited to these embodiments, and can include various modifications within the scope of the spirit of the present invention and the claims.

What is claimed is:

1. A meridian point-probing device, comprising:

a pulse wave-detecting unit which detects pulse waves;

a stimulation unit having an end that stimulates a position of skin of a trial subject;

a memory unit which stores pulse waveforms detected by the pulse wave-detecting unit before and after the stimulation of the position by the stimulation unit; and a meridian point determination unit which determines whether the stimulated position is a meridian point, according to the pulse waveforms stored in the memory unit, the meridian point determination unit including a waveform parameter calculation subunit that calculates a pressure parameter based on a point located on the pulse waveforms and determines whether the stimulated position is a meridian point, according to the pressure parameter.

2. A meridian point-probing device, comprising:

a pulse wave-detecting unit which detects pulse waves;

a stimulation unit having an end that stimulates skin of a trial subject;

a memory unit which stores pulse waveforms detected by the pulse wave-detecting unit after the stimulation of a plurality of positions of the skin of the trial subject by the stimulation unit; and a meridian point determination unit which determines whether each of the stimulated positions is a meridian point, according to the pulse waveforms stored in the memory unit, the meridian point determination unit including a waveform parameter calculation subunit that calculates a pressure parameter based on a point located on the pulse waveforms and determines whether the stimulated position is a meridian point, according to the pressure parameter.

3. The meridian point-probing device according to claim 2, wherein the waveform parameter calculation subunit calculates the pressure parameter that includes at least one of a pulse pressure that is a differential pressure between a systolic blood pressure and a diastolic blood pressure, a post-ejection pressure that is a differential pressure between a blood pressure at a dicrotic notch and the systolic blood pressure, a dicrotic wave height that is a differential pressure between the blood pressure at the dicrotic notch and a maximum blood pressure of the dicrotic wave, a post-ejection pressure ratio that corresponds to the post-ejection pressure normalized by the pulse pressure, a dicrotic wave height ratio that corresponds to the dicrotic wave height normalized by the pulse pressure, a tidal wave height ratio that corresponds to the tidal wave height normalized by the pulse pressure wherein the tidal wave height is a differential pressure between the blood pressure of the post-ejection pressure and a maximum blood pressure of a tidal wave, or a pulse from the pulse waveforms stored in the memory unit.

* * * * *